US008383390B2

(12) United States Patent
Koga et al.

(10) Patent No.: US 8,383,390 B2
(45) Date of Patent: Feb. 26, 2013

(54) BACTERIA THAT REDUCE CONTENT OF HEAVY METALS IN PLANT

(75) Inventors: Kazuharu Koga, Tokyo (JP); Shingo Masuda, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 64 days.

(21) Appl. No.: 12/949,991

(22) Filed: Nov. 19, 2010

(65) Prior Publication Data

US 2011/0136199 A1 Jun. 9, 2011

Related U.S. Application Data

(63) Continuation of application No. PCT/JP2009/059058, filed on May 15, 2009.

(30) Foreign Application Priority Data

May 29, 2008 (JP) ................. 2008-141201

(51) Int. Cl.
*C12N 1/20* (2006.01)
*C12N 1/00* (2006.01)
*A01N 63/00* (2006.01)
(52) U.S. Cl. ............ 435/252.1; 435/262; 435/267; 435/822; 504/117
(58) Field of Classification Search .................. None
See application file for complete search history.

(56) References Cited

U.S. PATENT DOCUMENTS

2007/0249034 A1 10/2007 Brigmon et al.

FOREIGN PATENT DOCUMENTS

| JP | 9-104606 A | 4/1997 |
|---|---|---|
| JP | 9-157122 A | 6/1997 |
| JP | 9-194314 A | 7/1997 |
| JP | 9-194316 A | 7/1997 |
| JP | 9-299076 A | 11/1997 |
| JP | 10-4954 A | 1/1998 |
| JP | 10-7483 A | 1/1998 |
| JP | 2005-137330 A | 6/2005 |
| JP | 2007-197421 A | 8/2007 |

OTHER PUBLICATIONS

Belimov et al. Canadian Journal of Microbiology, 2001, vol. 47, No. 7, pp. 642-652.*
Zaidi et al., "Significance of *Bacillus subtillis* strain SJ-101 as a bioinoculant for concurrent plant growth promotion and nickel accumulation in *Brassica juncea*", Chemosphere, vol. 64, 2006, pp. 991-997.
Abou-Shanab et al., "The Role of Bacteria on Heavy-Metals Extraction and Absorption by Plants Growing on Multi-Metal Contaminated Soils", The Egyptian Society of Experimental Biology (Botany), Vol. 2, 2006, pp. 1-6.
Belimov et al., "Cadmium-tolerant plant growth-promoting bacteria associated with the roots of Indian mustard (*Brassica juncea* L. Czern.)", Soil Biology and Biochemistry, vol. 37, No. 2, 2005, pp. 241-250.
Bruins et al., "*Pseudomonas pickettii*: A Common Soil and Groundwater Aerobic Bacteria with Pathogenic and Biodegradation Properties", Ecotoxicology and Environmental Safety, vol. 47, No. 2, 2000, pp. 105-111.
Chovanová et al., "Identification and characterization of eight cadmium resistant bacterial isolates from a cadmium-contaminated sewage sludge", Biologia, Bratislava, vol. 59, No. 6, 2004, pp. 817-827.
De et al., "Bioremediation of toxic substances by mercury resistant marine bacteria", Ecotoxicology, vol. 15, No. 4, May 2006, pp. 385-389.
De et al., "Characterization of marine bacteria highly resistant to mercury exhibiting multiple resistances to toxic chemicals", Ecological Indicators, vol. 7, No. 3, 2007, pp. 511-520.
Dell'Amico et al., "Improvement of *Brassica napus* growth under cadmium stress by cadmium-resistant rhizobacteria", Soil Biology & Chemistry, vol. 40, 2008, pp. 74-84.
Hassen et al., "Resistance of Environmental Bacteria to Heavy Metals", Bioresource Technology, vol. 64, No. 1, 1998, pp. 7-15.
Honma et al., "The possibility on the bacterial accumulation of cadmium", Bulletin of Tokyo Gakugei University Natural Sciences, vol. 58, 2006, pp. 127-130.
Janoušvoká et al., "Effects of arbuscular mycorrhizal inoculation on cadmium accumulation by different tobacco (*Nicotiana tabacum* L.) types", Applied Soil Ecology, vol. 35, 2007, pp. 502-510.
Madhaiyan et al., Metal tolerating methylotrophic bacteria reduces nickel and cadmium toxicity and promotes plant growth of tomato (*Lycopersicon esculentum* L.), Chemosphere, vol. 69, No. 2, 2007, pp. 220-228.
Mondal et al., "Treatment of arsenic contaminated water in a batch reactor by using *Ralstonia eutropha* MTCC 2487 and granular activated carbon", Journal of Hazardous Materials, vol. 153, 2008, pp. 588-599.
Nies et al., "Ion efflux systems involved in bacterial metal resistances", Journal of Industrial Microbiology, vol. 14, 1995, pp. 186-199.
Nies, "Microbial heavy-metal resistance", Applied Microbiology and Biotechnology, vol. 51, 1999, pp. 730-750.
Ozdemir et al., "Heavy metal biosorption by biomass of *Ochrobactrum anthropi* producing exopolysaccharide in activated sludge", Bioresource Technology, vol. 90, No. 1, 2003, pp. 71-74.
Rivera-Becerril et al., "Cadmium accumulation and buffering of cadmium-induced stress by arbuscular mycorrhiza in three *Pisum sativum* L. genotypes", Journal of Experimental Botany, vol. 35, No. 371, May 2002, pp. 1177-1185.
Sheng et al., "Characterization of heavy metal-resistant endophytic bacteria from rape (*Brassica napus*) roots and their potentail in promoting the growth and lead accumulation of rape", Environmental Pollution, vol. 156, 2008, pp. 1164-1170.
Sheng et al., "Improvement of rape (*Brassica napus*) plant growth and cadmium uptake by cadmium-resistant bacteria", Chemosphere, vol. 64, 2006, pp. 1036-1042.

(Continued)

*Primary Examiner* — Vera Afremova
(74) *Attorney, Agent, or Firm* — Birch, Stewart, Kolasch & Birch, LLP

(57) ABSTRACT

This invention relates to bacteria having a function of reducing the content of heavy metals in plants, a method for reducing the content of heavy metals in plants with the use of such bacteria, and a composition comprising, as an active ingredient, such bacteria.

8 Claims, No Drawings

OTHER PUBLICATIONS

Stephanauskas et al., "Coselection for microbial resistance to metals and antibiotics in freshwater microcosms", Environmental Microbiology, vol. 8, No. 9, 2006, pp. 1510-1514.

Tibazarwa et al., "Regulation of the cnr Cobalt and Nickel Resistance Determinant of *Ralstonia eutropha* (*Alcaligenes eutrophus*) CH34", Journal of Bacteriology, vol. 182, No. 5, Mar. 2000, pp. 1399-1409.

Zaidi et al., "Significance of *Bacillus subtilis* strain SJ-101 as a bioinoculant for concurrent plant growth promotion and nickel accumulation in *Brassica juncea*", Chemosphere, vol. 64, 2006, pp. 991-997.

* cited by examiner

```
SEQUENCE LISTING

<160> NUMBER OF SEQ ID NOS: 6

<210> SEQ ID NO 1
<211> LENGTH: 478
<212> TYPE: DNA
<213> ORGANISM: Ralstonia mannitolilytica

<400> SEQUENCE: 1
aacgctggcg gcatgcctta cacatgcaag tcgaacggca gcggggagag agcttgcttc      60
tcctgccggc gagtggcgaa cgggtgagta atacatcgga acgtgccctg tagtggggga    120
taactagtcg aaagattagc taataccgca tacgacctga gggtgaaagt ggggaccgc     180 aaggcctcat gctataggag cggccgatgt ctgattagct agttggtggg gtaaaggccc    240
accaaggcga cgatcagtag ctggtctgag aggacgatca gccacactgg gactgagaca    300
cggcccagac tcctacggga ggcagcagtg ggaattttg  acaatgggc gaaagcctga    360 tccagcaatg ccgcgtgtgt gaagaaggcc ttcgggttgt aaagcacttt tgtccggaaa    420
gaaatggctc tggttaatac ctggggtcga tgacggtacc ggaagaataa ggaccggc     478

<210> SEQ ID NO 2
<211> LENGTH: 476
<212> TYPE: DNA
<213> ORGANISM: Ralstonia mannitolilytica

<400> SEQUENCE: 2
ctggcggcat gccttacaca tgcaagtcga acggcagcgg gggagaagct tgcttctcct     60
gccggcgagt ggcgaacggg tgagtaatac atcggaacgt gccctgtagt gggggataac    120
tagtcgaaag attagctaat accgcatacg acctgagggt gaaagtgggg gaccgcaagg    180
cctcatgcta taggagcggc cgatgtctga ttagctagtt ggtggggtaa agcccacca    240 aggcgacgat cagtagctgg tctgagagga cgatcagcca cactgggact gagacacggc    300
ccagactcct acgggaggca gcagtgggga atttggaca atgggcgaaa gcctgatcca    360
gcaatgccgc gtgtgtgaag aaggccttcg ggttgtaaag cacttttgtc cggaaagaaa    420
tggctctggt taatacctgg ggtcgatgac ggtaccggaa gataaggac cggcta       476

<210> SEQ ID NO 3
<211> LENGTH: 472
<212> TYPE: DNA
<213> ORGANISM: Ralstonia pickettii
```

```
<400> SEQUENCE: 3
tggcggcatg ccttacacat gcaagtcgaa cggcagcatg atctagcttg ctagattgat      60
ggcgagtggc gaacgggtga gtaatacatc ggaacgtgcc ctgtagtggg ggataactag     120
tcgaaagatt agctaatacc gcatacgacc tgagggtgaa agtgggggac cgcaaggcct     180
catgctatag gagcggccga tgtctgatta gctagttggt ggggtaaagg cccaccaagg     240
cgacgatcag tagctggtct gagaggacga tcagccacac tgggactgag acacggccca     300
gactcctacg ggaggcagca gtggggaatt ttggacaatg ggcgaaagcc tgatccagca     360
atgccgcgtg tgtgaagaag gccttcgggt tgtaaagcac ttttgtccgg aaagaaatgg     420
ctctggttaa tacctggggt cgatgacggt accggaagaa taaggaccgg ct             472

<210> SEQ ID NO 4
<211> LENGTH: 478
<212> TYPE: DNA
<213> ORGANISM: Ralstonia pickettii

<400> SEQUENCE: 4
acsctggcgg catgccttac acatgcaagt cgaacggcag catgatctag cttgctagat      60
tgatggcgag tggcgaacgg gtgagtaata catcggaacg tgccctgtag tggggataa     120 ctagtcgaaa gattagctaa taccgcatac gacctgaggg tgaaagtggg ggaccgcaag     180
gcctcatgct ataggagcgg ccgatgtctg attagctagt tggtggggta aggcccacc     240 aaggcgacga tcagtagctg gtctgagagg acgatcagcc acactgggac tgagacacgg     300
cccagactcc tacgggaggc agcagtgggg aattttggac aatgggcgaa agcctgatcc     360
agcaatgccg cgtgtgtgaa gaaggccttc ggggttgtaaa gcacttttgt ccggaaagaa     420
atggctctgg ttaatacctg gggtcgatga cggtaccgga gaataagga ccggctaa       478

<210> SEQ ID NO 5
<211> LENGTH: 472
<212> TYPE: DNA
<213> ORGANISM: Variovorax paradoxus

<400> SEQUENCE: 5
cgctggcggc atgccttaca catgcaagtc gaacggcagc gcgggagcaa tcctggcggc      60
gagtggcgaa cgggtgagta atacatcgga acgtgcccaa tcgtggggga taacgcagcg     120
aaagctgtgc taataccgca tacgatctac ggatgaaagc aggggatcgc aagaccttgc     180
gcgaatggag cggccgatgg cagattaggt agttggtgag gtaaaggctc accaagcctt     240
cgatctgtag ctggtctgag aggacgacca gccacactgg gactgagaca cggcccagac     300
tcctacggga ggcagcagtg ggaattttg gacaatgggc gaaagcctga tccagccatg     360
ccgcgtgcag gatgaaggcc ttcggggttgt aaactgcttt tgtacggaac gaaacggcct     420
tttctaataa agagggctaa tgacggtacc gtaagaataa gcaccggcta ay              472

<210> SEQ ID NO 6
<211> LENGTH: 471
<212> TYPE: DNA
<213> ORGANISM: Cupriavidus necator

<400> SEQUENCE: 6
cgctggcggc atgccttaca catgcaagtc gaacggcagc acggggcaa ccctggtggc      60 gagtggcgaa cgggtgagta atacatcgga acgtgccctg tagtggggga taactagtcg     120
aaagattagc taataccgca tacgacctga gggtgaaagc ggggaccgt aaggcctcgc     180
```

-continued

| | | | | | |
|---|---|---|---|---|---|
| gctacaggag | cggccgatgt | ctgattagct | agttggtggg | gtaaaagcct | accaaggcga | 240 |
| cgatcagtag | ctggtctgag | aggacgatca | gccacactgg | gactgagaca | cggcccagac | 300 |
| tcctacggga | ggcagcagtg | gggaattttg | gacaatgggg | gcaaccctga | tccagcaatg | 360 |
| ccgcgtgtgt | gaagaaggcc | ttcggttgt | aaagcacttt | tgtccggaaa | gaaatggctc | 420 |
| tggttaatac | ctggggtcga | tgacggtacc | ggaagaataa | gcaccggcta | a | 471 |

BACTERIA THAT REDUCE CONTENT OF HEAVY METALS IN PLANT

This application is a Continuation of copending PCT International Application No. PCT/JP2009/059058 filed on May 15, 2009, which claims the benefit of Japanese Patent Application No. 2008-141201 filed in Japan on May 29, 2008. The entire content of each of the above documents is hereby incorporated by reference into the present application.

TECHNICAL FIELD

The present invention relates to bacteria that reduce the content of heavy metals in plants, a method for reducing the content of heavy metals in plants with the use of such bacteria, and a composition comprising, as an active ingredient, such bacteria.

BACKGROUND ART

Heavy metals such as cadmium and lead contained in natural substances such as minerals and soil have been discharged into the environment by human activities such as mine development.

For example, cadmium is contained in mine water, discharged water or smoke from a smelter, and wastewater from gob deposits, and such cadmium is a major cause of soil contamination at present. Also, cadmium is imported and produced in Japan, and it has been used for nickel-cadmium batteries, pigments, alloys, and a polyvinyl chloride stabilizer in the past. In the past, it was discharged into rivers and the air as discharged water or smoke from factories and incineration plants. Further, it is known that cadmium invades soil in croplands with the incursion from river water or the environment such as through rain water that has been contaminated with cadmium.

Some cadmium contained in food is absorbed by and accumulated in the body upon food ingestion. Accordingly, the Ministry of Health, Labor and Welfare has announced that long-term ingestion of food with high cadmium content may cause renal dysfunction. In addition, cases of itai-itai disease have been caused by environmental cadmium contamination in Japan.

The international standards for food cadmium content have been under review by the Codex Alimentarius Commission since 1998. The Codex Alimentarius Commission announced international standards in July 2007, such as 0.4 mg of cadmium per kg of polished rice and 0.2 mg thereof per kg of wheat.

The cadmium content in crops can be reduced via, for example, introduction of soil dressing or soil improvement agents, utilization of a plant variety having a low capacity for cadmium absorption, or soil cleanup via phytoremediation or soil washing.

At present, soil improvement is mainly carried out by a method involving soil dressing. This method, however, requires tremendous amounts of money, and it is difficult to collect the amount of mountain soil required for soil dressing. In addition, soil dressing necessitates the disposal of large quantities of waste soil. Further, it is necessary to improve soil so that it will be suitable for crop cultivation. When the depth of soil dressing is insufficient, contamination may occur again. Thus, development of a technique that is sufficient in respect of physical and economical conditions has been awaited. Other techniques also require tremendous amounts of money and time.

Removal of cadmium from the environment with the aid of microorganisms is expected as a cost-effective technique. Metal cations are bound to anions, such as sulfide ions or hydroxide ions, and converted into hardly-soluble compounds in water. Sulfides, hydroxides, phosphates, and the like of heavy metal ions are insoluble or hardly-soluble in water. With the utilization of such properties, removal of cadmium from the environmental water has been attempted using microorganisms. As microorganisms that precipitate sulfides, sulfate-reducing bacteria of the genus *Desulfovibrio* and the like are known. It is known that such microorganisms are distributed in lakes, wetlands, or rice paddies in which large quantities of organic matter exist, and research regarding the reduction of heavy metals in paddy rice has been conducted. While such microorganisms are effective for rice cultivated in rice paddies, sulfides are converted into sulfuric acids, which are absorbable by crops in fields under acidic conditions. Thus, such microorganisms cannot be used in fields under acidic conditions.

It was reported that the cadmium concentration in the roots of garden peas was lowered via treatment with the use of mycorrhizal fungi. Mycorrhizal fungus is known to infect roots of a specific host and accelerate the nutrient absorption of plants, and particularly phosphoric acid absorption. However, the effects of cadmium reduction were not observed in soil containing highly concentrated cadmium (Journal of Experimental Botany, 2002, 53, pp. 1177-1185).

Also, an attempt to reduce cadmium in tobacco with the use of mycorrhizal fungi of the genus *Glomus* was reported (Applied Soil Ecology, 2007, 35, pp. 502-510). The effects of cadmium reduction in leaves were observed in 3 Arbuscular Mycorrhiza (AM). However, no correlation has been observed between the effects of cadmium reduction and colonization of mycorrhizal fungi. AM are mold species, which are difficult to artificial culture, and mass culture thereof is laborious and time-consuming. Further, mycorrhizal fungi only colonize roots of a specific host and it is difficult to use them except their host. Functions of mycorrhizal fungi are known to differ significantly depending on the soil, and the functions thereof are known to be suppressed in soil that is rich in phosphoric acid or soil that is poor in air permeability. Thus, the effects of cadmium reduction may significantly vary depending on soil. Also, the experiment of Applied Soil Ecology, 2007, 35, pp. 502-510 was performed only in a greenhouse, and soil immediately after sterilization was used. When sterilized soil is used, it is deduced that microorganisms added via inoculation become the dominant species in such soil. When plants are cultivated, in general, a wide variety of microorganisms exist in soil, and the amounts of inoculated microorganisms decrease via nutrient competition, for example. Thus, it is important to conduct an experiment under environments in which plants are actually cultivated, such as in fields.

Bacteria have been heretofore used as control agents of soil-borne diseases or plant diseases.

For example, *Ochrobactrum anthropi* TRB19 strain is used as a control agent of a soil disease for Solanaceous plants, and this strain exhibits the effects of controlling bacterial wilt disease against Solanaceous plants including tobacco and tomato upon application thereof to roots, cultivation area, and/or soil used for cultivation of Solanaceous plants (JP Patent Publication (kokai) No. H09-194314 A (1997)).

*Alcaligenes faecalis* (Accession Number: FERM P-15229) is used as a control agent of a plant disease for cucumbers, and it is used for a method in which the culture product of such bacteria or bacteria cell are suspended in water and the resulting suspension is sprayed on plants or a method in which it is sprayed on foliage aimed at controlling foliar diseases, such as powdery mildew (JP Patent Publication (kokai) No. H09-104606 A (1997)).

A bacterial strain of the genus *Variovorax* (CGF4526, Accession Number: FERM P-19563) is used as a control agent for the clubroot disease of Brassicaceae plants, and such control agent comprising the strain is mixed with soil or subjected to perfusion of soil when seedlings are raised, or seedlings are soaked in the control agent before being planted in the field (JP Patent Publication (kokai) No. 2005-137330 A).

In addition, a combination of the bacterial strain of the genus *Variovorax* (CGF4526) and nonpathogenic *Erwinia carotovora* subsp. *carotovora* is used as a control agent for the clubroot disease of Brassicaceae plants, and such control agent is applied when raising seedlings (i.e., before transplantation to the main field) (JP Patent Publication (kokai) No. 2007-197421 A).

SUMMARY OF THE INVENTION

Object of the Invention

It is an object of the present invention to provide bacteria having a function of reducing the content of heavy metals in plants, a method for reducing the content of heavy metals in plants with the use of such bacteria, and a composition comprising, as an active ingredient, such bacteria.

Means for Attaining the Object

The present inventors have conducted concentrated studies in order to attain the above object. As a result, they succeeded in isolating bacteria having a function of reducing the content of heavy metals such as cadmium in plants. This has led to the completion of the present invention.

The present invention is summarized as follows.

(1) A bacterium belonging to the genus *Ochrobactrum*, the genus *Alcaligenes*, the genus *Ralstonia*, the genus *Variovorax*, the genus *Cupriavidus*, the genus *Burkholderia*, or the genus *Stenotrophomonas* and having a function of reducing the content of heavy metals in a plant.

(2) The bacterium according to (1), wherein the heavy metal is selected from the group consisting of cadmium, copper, lead, chromium, nickel, and arsenic.

(3) The bacterium according to (1) or (2), which is *Ochrobactrum anthropi*, *Alcaligenes xylosoxidans*, *Alcaligenes faecalis*, *Ralstonia mannitolilytica*, *Ralstonia pickettii*, *Variovorax paradoxus*, *Cupriavidus necator*, *Burkholderia cepacia*, or *Stenotrophomonas maltophilia*.

(4) The bacterium according to any of (1) to (3), which is *Ochrobactrum anthropi* JHA60 strain (Accession Number: NITE BP-549), *Alcaligenes xylosoxidans* JHB14 strain (Accession Number: NITE BP-550), *Alcaligenes faecalis* JHC10 strain (Accession Number: NITE BP-551), *Ralstonia mannitolilytica* JHG2 strain (Accession Number: NITE BP-552), *Ralstonia mannitolilytica* JHL8 strain (Accession Number: NITE BP-554), *Ralstonia pickettii* JHP30 strain (Accession Number: NITE BP-555), *Ralstonia pickettii* JHP55 strain (Accession Number: NITE BP-557), *Variovorax paradoxus* JHP31 strain (Accession Number: NITE BP-556), or *Cupriavidus necator* JHJ6 strain (Accession Number: NITE BP-553).

(5) The bacterium according to any of (1) to (4), which is immobilized on a carrier.

(6) A method for reducing the content of heavy metals in a plant comprising applying at least one bacterium according to any of (1) to (5) to a root of a plant or soil around plant roots.

(7) The method according to (6), wherein the applying is carried out at least once during the period from sowing to post-transplanting in the field.

(8) The method according to (6) or (7), wherein the applying is carried out by directly applying the bacterium to the root, or by adding or mixing the bacterium to/with soil around the root or to/with a hydroponic solution.

(9) The method according to any of (6) to (8), wherein the plant is selected from the group consisting of plants of Solanaceae, Gramineae, Polygonaceae, Leguminosae, Brassicaceae, Liliaceae, Compositae, and Chenopodiaceae families.

(10) A composition for reducing the content of heavy metals in a plant comprising, as an active ingredient, the bacterium according to any of (1) to (5).

The term "the root of a plant" used herein refers to a part of a plant that absorbs moisture or nutrient components in soil or a hydroponic solution at the time of plant cultivation.

The term "Accession Number" used herein refers to a number given upon deposition and receipt of bacteria of the present invention at the Patent Microorganisms Depositary (NPDM) of the National Institute of Technology and Evaluation (NITE) (2-5-8 Kazusakamatari, Kisarazu-shi, Chiba, 292-0818, Japan) (date of deposition: Apr. 10, 2008).

Effects of the Invention

The bacteria of the present invention having a function of reducing the content of heavy metals in plants are capable of reducing the content of heavy metals such as cadmium in plants and having resistance to heavy metals. The present invention is applicable to a variety of plants including plants of Gramineae, Polygonaceae, Leguminosae, Brassicaceae, Chenopodiaceae, Liliaceae, and Compositae, in addition to plants of Solanaceae such as tobacco. In addition, the frequency of application of the bacteria or composition of the present invention to the root of a plant, soil around the plant root, or a hydroponic solution may be increased so as to improve the effects of reducing the content of heavy metals in a plant.

The bacteria of the present invention having a function of reducing the content of heavy metals in plants can be multiplied via liquid culture or other means in an easier manner than mycorrhizal fungi. Plant root colonization of mycorrhizal fungi is significantly influenced by components, conditions, or other conditions of soil; however, that of the bacteria is considered to be influenced by supply of nutrients from the plant root rather than components, conditions, or other conditions of soil. In addition, the bacteria of the present invention have a broad host range compared with mycorrhizal fungi. Thus, the bacteria of the present invention are considered to have high versatility in terms of colonization to plants and applicability to a variety of plants. The effects of the present invention for reducing the content of heavy metals in plants have been confirmed in the field, as well as in a greenhouse.

This description contains part or all of the contents as disclosed in the description and/or drawings of Japanese Patent Application No. 2008-141201, based on which the present application claims priority.

BEST MODES FOR CARRYING OUT THE INVENTION (1) Bacteria of the Present Invention

The bacteria of the present invention have a function of reducing the content of heavy metals in plants and belong to the genus *Ochrobactrum*, the genus *Alcaligenes*, the genus *Ralstonia*, the genus *Variovorax*, the genus *Cupriavidus*, the genus *Burkholderia*, the genus *Stenotrophomonas*, the genus *Pseudomonas*, the genus *Bacillus*, the genus *Flavobacterium*, or the genus *Sphingomonas*. Specific examples of the bacteria of the present invention include *Ochrobactrum anthropi, Alcaligenes xylosoxidans, Alcaligenes faecalis, Ralstonia mannitolilytica, Ralstonia pickettii, Variovorax paradoxus, Cupriavidus necator, Burkholderia cepacia,* and *Stenotrophomonas maltophilia. Ochrobactrum anthropi* JHA60 strain (Accession Number: NITE BP-549), *Alcaligenes xylosoxidans* JHB14 strain (Accession Number: NITE BP-550), *Alcaligenes faecalis* JHC10 strain (Accession Number: NITE BP-551), *Ralstonia mannitolilytica* JHG2 strain (Accession Number: NITE BP-552), *Ralstonia mannitolilytica* JHL8 strain (Accession Number: NITE BP-554), *Ralstonia pickettii* JHP30 strain (Accession Number: NITE BP-555), *Ralstonia pickettii* JHP55 strain (Accession Number: NITE BP-557), *Variovorax paradoxus* JHP31 strain (Accession Number: NITE BP-556), and *Cupriavidus necator* JHJ6 strain (Accession Number: NITE BP-553) are particularly preferable.

The bacteria of the present invention may be immobilized on carriers. Examples of carriers include known carriers that can be used for bacterial immobilization such as active carbon, diatomaceous earth, zeolite, peat moss, pearlite, bentonite, montmorillonite, vermiculite, alumina, silicate, crystalline cellulose, corn starch, gelatin, and alginic acid. Bacteria may be adsorbed on carriers to prepare immobilized bacteria.

The term "heavy metal" used herein refers to a metallic element having a specific gravity of at least 4 to 5.

Heavy metals that can be reduced by the bacteria of the present invention are not particularly limited, and examples thereof include cadmium, copper, lead, chromium, nickel, arsenic, mercury, manganese, cobalt, selenium, bismuth, and iron. Examples of preferable heavy metals include cadmium, copper, lead, chromium, nickel, and arsenic.

The bacteria of the present invention can be isolated from general soil such as that in the field. For example, the root of a plant from which soil has been removed is added into a buffer (e.g., a Tris buffer at around neutral) and shaken to obtain a suspension for separating bacteria in rhizospheric soil. The resulting suspension is applied to a microbial medium supplemented with a heavy metal such as cadmium (e.g., a triptic soy agar medium), bacteria are cultured, and grown colonies are isolated. The colonies are cultured in a medium supplemented with a heavy metal and in a medium free of a heavy metal, the growth conditions are compared, and heavy-metal-resistant bacteria exhibiting equivalent to somewhat poor growth conditions in a medium supplemented with a heavy metal are selected. Plants to which the selected bacteria are applied at the roots and plants to which such bacteria are not applied are grown in soil supplemented with a heavy metal. The plants are recovered, and the content of heavy metals in plants is determined with the use of, for example, an inductively coupled plasma mass spectrometer (ICP-MS) (ICPM-8500, Shimadzu Corporation). When the heavy metal concentration in a plant to which bacteria have been applied has been significantly reduced compared with that of a plant to which bacteria have not been applied, such bacteria are designated as having a function of reducing the content of heavy metals in a plant. In addition, such bacteria have resistance to heavy metals. The term "resistance to heavy metals" refers that bacteria can be multiplied in the presence of heavy metals.

The thus-obtained bacteria can be multiplied via a general technique. Culture is preferably carried out under aerobic conditions, for example, the bacteria of the present invention are inoculated into an inorganic or organic nutrient medium containing inorganic salts (e.g., phosphoric acid salts, magnesium salts, calcium salts, iron salts, ammonium salts, or salts of trace metals), nitrogen sources (e.g., ammonia, nitrate salts, nitrite salts, or amino acids), and other nutrients (e.g., bases), and culture is conducted via shaking or aerobic spinner culture. Culture may be conducted within a temperature range in which bacteria to be cultured can grow, and the temperature can be set preferably between 20° C. and 40° C., and more preferably between 25° C. and 30° C. The pH level of a medium may be in a range in which bacteria to be cultured can grow, and the pH level can be set preferably between 6.0 and 8.0 and more preferably between 6.5 and 7.5. The culture duration is not particularly limited, and it is preferably 24 hours to 3 days.

(2) Identification of Bacteria

The bacteria of the present invention were identified in terms of mycological properties based on morphological and bacteriological properties, physiological and biochemical properties determined with the use of a kit for identifying gram-negative rod-shaped bacteria (API20NE; manufactured by BioMe'rieux) and a homology comparison of 16S rRNA nucleotide sequences, and the like. Mycological properties of the bacteria of the present invention are shown in Table 1 to Table 7.

(i) JHA60 strain (Accession Number: NITE BP-549)

TABLE 1

Mycological properties based on morphological properties and basic properties of JHA60 strain

| Test items | |
|---|---|
| Morphology (Cell shape) | Rod |
| Gram reaction | − |
| Spore formation | − |
| Motility | + |
| Growth under oxygen | Aerobic |
| Oxidase | + |
| Catalase | + |
| OF test | O |
| Color of colony | NP[1)] |

[1)]NP: No characteristic colony color tone was formed.

TABLE 2

Mycological properties of JHA60 strain determined via API20NE

| Test items | |
|---|---|
| Nitrate reduction | − |
| Indole test | − |
| Glucose fermentability | − |
| Arginine dihydrolase | − |
| Urease | − |
| Esculin hydrolysis | − |
| Gelatin liquefaction | − |
| β-galactosidase | − |
| Carbon sources for growth | |
| Glucose | + |
| L-arabinose | − |
| D-mannose | + |
| D-mannitol | + |
| N-acetyl-D-glucosamine | + |
| Maltose | + |
| Potassium gluconate | + |
| n-capric acid | − |
| Adipic acid | − |
| dl-malic acid | + |
| Sodium citrate | + |
| Phenyl acetate | − |
| Oxidase | + |

Based on the properties shown above, the JHA60 strain was identified as a strain of *Ochrobactrum anthropi*.

(ii) JHB14 strain (Accession Number: NITE BP-550)

TABLE 3

Mycological properties based on morphological properties and basic properties of JHB14 strain

| Test items | |
|---|---|
| Morphology (Cell shape) | Rod |
| Gram reaction | − |
| Spore formation | − |
| Motility | + |
| Growth under oxygen | Aerobic |
| Oxidase | + |
| Catalase | + |
| OF test | O |
| Color of colony | NP[1)] |

[1)]NP: No characteristic colony color tone was formed.

TABLE 4

Mycological properties of JHB14 strains determined via API20NE

| Test items | |
|---|---|
| Nitrate reduction | + |
| Indole test | − |
| Glucose fermentability | − |
| Arginine dihydrolase | − |
| Urease | − |
| Esculin hydrolysis | − |
| Gelatin liquefaction | − |
| β-galactosidase | − |
| Carbon sources for growth | |
| Glucose | + |
| L-arabinose | − |
| D-mannose | + |
| D-mannitol | − |
| N-acetyl-D-glucosamine | − |
| Maltose | − |
| Potassium gluconate | + |
| n-capric acid | + |
| Adipic acid | + |
| dl-malic acid | + |
| Sodium citrate | + |
| Phenyl acetate | + |
| Oxidase | + |

Based on the properties shown above, the JHB14 strain was identified as a strain of *Alcaligenes xylosoxidans*.

(iii) JHC10 strain (Accession Number: NITE BP-551)

TABLE 5

Mycological properties based on morphological properties and basic properties of JHC10 strains

| Test items | |
|---|---|
| Morphology (Cell shape) | Rod |
| Gram reaction | − |
| Spore formation | − |
| Motility | + |
| Growth under oxygen | Aerobic |
| Oxidase | + |
| Catalase | + |
| OF test | − |
| Color of colony | NP[1)] |

[1)]NP: No characteristic colony color tone was formed.

TABLE 6

Mycological properties of JHC10 strain in terms of API20NE

| Test items | |
|---|---|
| Nitrate reduction | + |
| Indole test | − |
| Glucose fermentability | − |
| Arginine dihydrolase | − |
| Urease | − |
| Esculin hydrolysis | − |
| Gelatin liquefaction | − |
| β-galactosidase | − |
| Carbon sources for growth | |
| Glucose | − |
| L-arabinose | − |
| D-mannose | − |
| D-mannitol | − |
| N-acetyl-D-glucosamine | − |
| Maltose | − |
| Potassium gluconate | + |
| n-capric acid | + |
| Adipic acid | + |
| dl-malic acid | + |
| Sodium citrate | + |
| Phenyl acetate | + |
| Oxidase | + |
| Additional test | |
| Generation of acid from xylose | − |
| Assimilability of fructose | − |
| Growth in the presence of 4% NaCl | − |
| Hydrolysis of Tween 80 | − |

Based on the properties shown above, the JHC10 strain was identified as a strain of *Alcaligenes faecalis*.

(iv) JHG2 strain (Accession Number: NITE BP-552), (v) JHL8 strain (Accession Number: NITE BP-554), (vi) JHP30 strain (Accession Number: NITE BP-555), (vii) JHP55 strain (Accession Number: NITE BP-557), (viii) JHP31 strain (Accession Number: NITE BP-556), and (ix) JHJ6 strain (Accession Number: NITE BP-553)

Mycological properties of strains (iv) to (ix) are shown in Table 7.

TABLE 7

Mycological properties of strains based on morphological properties and basic properties

| Test items | JHG2 | JHL8 | JHP30 | JHP55 | JHP31 | JHJ6 |
|---|---|---|---|---|---|---|
| Morphology (Cell shape) | Rod | Rod | Rod | Rod | Rod | Rod |
| Gram reaction | − | − | − | − | − | − |

TABLE 7-continued

Mycological properties of strains based on morphological properties and basic properties

| Test items | JHG2 | JHL8 | JHP30 | JHP55 | JHP31 | JHJ6 |
|---|---|---|---|---|---|---|
| Spore formation | − | − | − | − | − | − |
| Motility | + | + | + | + | + | + |
| Growth under oxygen | Aerobic | Aerobic | Aerobic | Aerobic | Aerobic | Aerobic |
| Oxidase | + | + | + | + | + | + |
| Catalase | + | + | + | + | + | + |
| OF test | − | O | O | O | − | O |
| Color of colony | NP | NP | NP | NP | Yellow | NP |

NP: No characteristic colony color tone was formed.

Bacteria (iv) to (ix) were identified based on nucleotide sequences. DNAs of bacteria (iv) to (ix) were extracted, DNA sequences of 16S rRNA regions were analyzed via PCR, homology search was conducted using known nucleotide sequence databases, and dendrograms thereof with related species were prepared. Table 8 shows the results of homology search of (iv) to (ix), and Table 9 shows the results of identification of (iv) to (ix) and sequence identification numbers (1 to 6) of the DNA sequences of the 16S rRNA regions. Based on such results, the JHG2 strain and the JHL8 strain were identified as of *Ralstonia mannitolilytica*, the JHP30 strain and the JHP55 strain were identified as of *Ralstonia pickettii*, the JHP31 strain was identified as of *Variovorax paradoxus*, and the JHJ6 strain was identified as of *Cupriavidus necator*.

TABLE 8

Results of homology search of strains

| Strain | Target species | % Match |
|---|---|---|
| JHG2 | *Ralstonia mannitolilytica* <AJ270258> | 98.76 |
| JHL8 | *Ralstonia mannitolilytica* <AJ270258> | 98.65 |
| JHP30 | *Ralstonia pickettii* | 99.54 |
| JHP55 | *Ralstonia pickettii* | 99.51 |
| JHP31 | *Variovorax paradoxus* | 100.00 |
| JHJ6 | *Cupriavidus necator* | 98.28 |

Notations within parentheses represent GenBank Accession Numbers.

TABLE 9

Results of identification of strains

| Strain | Species | SEQ ID NO: |
|---|---|---|
| JHG2 | *Ralstonia mannitolilytica* | 1 |
| JHL8 | *Ralstonia mannitolilytica* | 2 |
| JHP30 | *Ralstonia pickettii* | 3 |
| JHP55 | *Ralstonia pickettii* | 4 |
| JHP31 | *Variovorax paradoxus* | 5 |
| JHJ6 | *Cupriavidus necator* | 6 |

(3) Method for Reducing Heavy Metal Content in Plant

In order to realize bacterial density that is different from the natural state in the root of a plant or in soil around the plant root, a certain amount or more bacteria of the present invention are used. This can reduce the content of heavy metals in plants as a consequence. A single type of bacteria may be used, a plurality of types of bacteria may be used in combination, or immobilized bacteria may be used.

Target plants of the present invention are not particularly limited. Examples thereof include: Gramineae plants such as rice, barley, wheat, maize, Sorghum bicolor, and sugar cane; Polygonaceae plants such as buckwheat; Solanaceae plants such as tobacco, eggplant, tomato, pimento, and capsicum; Leguminosae plants such as soybean, *Phaseolus angularis*, horse bean, and garden pea; Brassicaceae plants such as cabbage, Chinese cabbage, cauliflower, broccoli, Japanese radish, turnip, *Brassica chinensis komatsuna*, *Brassica campestris*, *Brassica rapa* var. *nipposinica*, *Brassica juncea*, and *Brassica rapa* var. *chinensis*; Chenopodiaceae plants such as spinach and beet; Compositae plants such as lettuce and butterhead lettuce; and Liliaceae plants such as *Allium fistulosum* and *Allium tuberosum*.

The bacteria of the present invention may be applied to a root of a plant or soil around the plant root by directly applying the bacteria to the root, or by adding or mixing bacteria to/with soil around the root or to/with a hydroponic solution. Examples of soil types include every type of soil used for plant cultivation, such as molds used for sowing, soil used for cultivation, and soil and culture soil containing fertilizers.

Methods of applying bacteria are not particularly limited, and examples of such methods include affusion or perfusion of a plant with a cell suspension, soaking of the root of a plant in such a suspension, incorporation or spraying of bacteria in soil used for plant cultivation, and mixing of bacteria with a hydroponic solution (in the case of hydroponic culture). It is preferable to perform affusion or perfusion so that the treated microorganisms sufficiently infiltrate the root of a plant or soil around the plant root. Specifically, bacteria may be brought into contact with the root of a plant.

Bacteria may be applied at any timing from the sowing to the end of cultivation of plants without particular limitation. It is preferable that bacteria be applied at least once before plants absorb heavy metals and such metals start to accumulate therein (i.e., during the period from sowing to post-transplantation to the field). The frequency of the applying is not limited to a single instance, and bacteria may be applied several times or continuously during the period of plant cultivation after sowing of plants, according to need. By applying bacteria several separate times, the effects of heavy metal reduction can be greater.

The amount of bacteria applied is $10^6$ cfu (colony-forming units) or more, preferably $10^7$ cfu or more, and more preferably $10^9$ cfu or more per plant, when plants are individually treated. The amount of bacteria applied varies to some extent depending on the stage of the plant growth.

The bacteria may be applied in any form, provided that such form is suitable for application of bacteria to soil, hydroponic solution, or the like. The cultured bacteria may be used without modification, or bacteria may be used in the form of a composition comprising such bacteria as active ingredients in combination with a carrier or carriers shown below. Examples of liquid carriers include, but are not particularly limited to, water and buffers. Examples of solid carriers include, but are not particularly limited to, active carbon, diatomaceous earth, zeolite, peat moss, pearlite, bentonite, montmorillonite, vermiculite, alumina, silicate, crystalline cellulose, corn starch, gelatin, and alginic acid. A single type of carrier may be used or a plurality of types of carriers may be used in combination. Bacteria may be suspended in, added to, or mixed with such carriers, a fixing agent, a dispersant, an auxiliary material, or the like may be adequately added thereto, and the resultant may be used in the form of, for example, powder, granules, water dispersible powder, a liquid drug, an emulsion, or a suspension.

The composition may comprise ingredients other than the aforementioned. Specifically, the composition may comprise ingredients that are useful for helping bacteria to grow, and examples of such ingredients include inorganic salts, nitrogen sources, other nutrients, sugars (e.g., glucose and sucrose), and organic materials (e.g., beef extract and yeast extract). Further, the composition may comprise ingredients that are useful for helping plants to grow (i.e., various types of fertilizers).

EXAMPLES

Hereafter, the present invention is described in greater detail with reference to the examples, although the technical scope of the present invention is not limited thereto.

Example 1

Isolation of Microorganism

Cadmium tolerant microorganisms were isolated from rhizospheric soils of cultivated tobacco and soils of tobacco fields in Tochigi, Iwate, Yamagata, Akita, Okinawa, and Aomori prefectures in Japan.

The soil suspension for isolating bacteria was prepared in the following method. To remove soils around roots sampled from cultivated tobacco, the roots were thoroughly shaken in air and mildly shaken in distilled water contained in a beaker. Roots from which an excess water had been lightly removed were added into a 500-ml triangular flask with a baffle containing 200 ml of 0.01M phosphate buffer (pH 7.0), and the flask was shaken for 15 minutes. Further, an excess water on the removed roots was lightly removed, the roots were added into another 500-ml triangular flask with a baffle containing 200 ml of 0.01M phosphate buffer (pH 7.0), and the flask was shaken for 30 minutes. The resulting solution was designated as a suspension for isolating bacteria from rhizospheric soil.

The prepared suspension used for separation was applied on a 10-fold-diluted triptic soy agar medium containing cadmium at 0.5 or 2.0 mM (Difco, Bacto Tryptic Soy Broth; i.e., a medium prepared by adding agar to a concentration of 1.5% to a soybean-casein digest medium; hereafter abbreviated as "1/10TS agar medium"). The medium applied suspension was cultured at 30° C. for 4 to 7 days, and the grown colonies were separated.

Cadmium tolerance of the separated bacteria was inspected in the following method. The separated bacteria were precultured on 1/10TS agar medium at 28° C. for 3 days, the cultured bacteria were scraped using a sterilized plastic loop, and the bacteria were suspended in sterile distilled water to a concentration of about $10^{10}$ cfu/ml. The suspension (1 μl) was streaked on 1/10TS agar medium supplemented with cadmium (cadmium concentration: 0.5, 2.0 mM) and culture was incubated at 28° C. for 10 days. Cadmium tolerance was inspected by visually comparing the growth conditions in a medium supplemented with cadmium and in a cadmium-free medium, and bacteria grown to equivalent to somewhat poor conditions compared with those grown in a cadmium-free medium were designated as tolerant strains. The microorganisms that had been confirmed to be cadmium tolerant were suspended in a 10% glycerin solution and stored at −80° C. before use.

The numbers of the isolated cadmium tolerant bacteria are shown in Table 10. From the soil of tobacco fields and rhizospheric soil of tobacco, 723 cadmium tolerant strains were isolated. The 723 isolated strains were tolerant to cadmium at a concentration of 0.5 or 2.0 mM.

TABLE 10

Source of microorganisms and number of isolated strains

| Soil sampling location | Source | Number of separated strains |
| --- | --- | --- |
| Tochigi Pref. | Rhizospheric soil | 115 |
| Iwate Pref. | Rhizospheric soil | 101 |
| Yamagata Pref. | Rhizospheric soil | 118 |
| Yamagata Pref. | Soil | 98 |
| Akita Pref. | Rhizospheric soil | 55 |
| Akita Pref. | Soil | 77 |
| Okinawa Pref. | Rhizospheric soil | 44 |
| Aomori Pref. | Soil | 115 |

Example 2

Selection of Bacteria that Reduce Cadmium in Leaves in Greenhouse I

Inoculums were prepared in the following method. The stored bacteria were precultured in 1/10TS agar medium at 28° C. for 3 days. The cultured bacteria were scraped with a sterilized plastic loop, inoculated into a 100-ml triangular flask containing 50 ml of triptic soy broth (Difco, Bacto Tryptic Soy Broth; i.e., soybean-casein digest medium; hereafter referred to as "TS liquid medium"), and broth inoculated by bacteria was then cultured by shaking at 28° C. for 48 hours. The bacterial culture solution was designated as an inoculum.

Selection soil was prepared in the following method. Sterilized greenhouse field soil (Akaboku soil), Akadama bonsai soil (small grains), and JT organic/chemical fertilizers for yellow species were mixed at a proportion of 9:1:0.1 by weight. A cadmium solution to be added to soil was prepared by dissolving cadmium chloride ($CdCl_2.2.5H_2O$; Wako Pure Chemical Industries, Ltd.) in 0.01% nitric acid. The cadmium solution was added to soil to realize a total cadmium concentration of about 2 ppm, and the resultants were designated as a selection soil.

Seedlings (at the 8- to 9-leaf stage) in conditions equivalent to those of a tobacco variety, Tsukuba 1, were used. The age of the seedlings was equivalent to that of the seedlings for transplanting to the main field. On the day before transplantation to the greenhouse, the bottom of tobacco seedlings grown in vinyl pots (36×36 holes) were subjected to perfusion with 50 ml of the bacterial culture solution (bacteria concentration: $10^9$ to $10^{10}$ cfu/ml; amount of bacteria used per strain: $10^{10}$ to $10^{11}$ cfu) per 3 strains. As a control, seedlings treated with sterile TS liquid medium were used. The inoculated seedlings were transplanted to the selection soil and cultured at 25° C. for 3 weeks.

Sampling was carried out in the following method. After the completion of cultivation, the 4th to the 6th leaves from the bottom were sampled from two tobacco plants as a sample (6 leaves in total). The sampled leaves were dried at 60° C. to 70° C., ground, and designated as samples for analysis. In this experiment, a sample was prepared for the each bacterial treatment, and four or five samples each were prepared for the control. The average cadmium concentration of four or five samples was determined as cadmium concentration of a control.

The cadmium concentration in leaves was determined by assaying the cadmium concentration in samples decomposed with the use of a microwave sample analyzer with an inductively coupled plasma mass spectrometer. Samples were degraded in the following method. The ground samples (0.1 g) were introduced into a Teflon decomposition vessel for microwaving, and 5 ml of nitric acid (for ultra micro-analysis, 148-06935, Wako Pure Chemical Industries, Ltd.) and 2 ml of a hydrogen peroxide solution (for atomic absorption, 085-04056, Wako Pure Chemical Industries, Ltd.) were further added. The decomposition vessel was hermetically sealed, and the samples were decomposed with the aid of a microwave analyzer (Multiwave 3000, Perkin Elmer Japan). The cadmium concentrations in the decomposed samples were analyzed with ICP-MS (ICPM-8500, Shimadzu Corporation). The cadmium concentrations in the bacteria-treated leaves and in the control tobacco leaves were determined.

Selection of effects of cadmium reduction via bacterial treatment in greenhouse I was evaluated as follows. The cadmium concentration in leaves of the control was compared with that of the bacterial treatment, and bacteria exhibiting reduction of 20% or higher as a result of treatment were selected.

Table 11 shows the results of selection in greenhouse I. From among the isolated cadmium tolerant bacteria, 114 bacterial strains exhibiting 20% or higher cadmium reduction in leaves via perfusion thereof at the bottom compared with the control were selected from isolated cadmium tolerant bacteria.

TABLE 11

Number of bacteria exhibiting effects of cadmium reduction in leaves

| Soil sampling location | Source | Number of bacteria exhibiting reduction |
| --- | --- | --- |
| Tochigi Pref. | Rhizospheric soil | 30 |
| Iwate Pref. | Rhizospheric soil | 22 |

TABLE 11-continued

Number of bacteria exhibiting effects of cadmium reduction in leaves

| Soil sampling location | Source | Number of bacteria exhibiting reduction |
| --- | --- | --- |
| Yamagata Pref. | Rhizospheric soil | 19 |
| Yamagata Pref. | Soil | 7 |
| Akita Pref. | Rhizospheric soil | 3 |
| Akita Pref. | Soil | 10 |
| Okinawa Pref. | Rhizospheric soil | 6 |
| Aomori Pref. | Soil | 17 |

Example 3

Selection of Bacteria that Reduce Cadmium in Leaves in Greenhouse II

Inoculums and selection soil were prepared in the same method as in Example 2.

Tobacco seedlings for experiment used in Example 2 were used herein. Perfusion of seedlings with bacteria was carried out in the same method as in Example 2.

Sampling was carried out in the same method as in Example 2, except that four or five samples each were prepared for the each bacterial treatment and for the control.

The cadmium concentrations in leaves were analyzed in the same method as in Example 2.

The effects of cadmium reduction via bacterial treatment in greenhouse II were evaluated in the following method. The cadmium concentration in leaves of the control and that of the bacterial treatment were statistically analyzed, and bacteria exhibiting the significantly reduced cadmium concentrations compared with the control group were selected.

The results of selection in greenhouse II are shown in Table 12. Bacteria exhibiting significantly reduced cadmium concentrations in leaves compared with the control as a result of perfusion of the bacteria at the bottom were selected. Six bacterial strains exhibited a significant reduction of 30% or higher and three bacterial strains exhibited reduction of 20% to 30% compared with the cadmium concentration in leaves of the control.

TABLE 12

Effects of reduction of cadmium in leaf by bacteria

| Strain number | Bacteria | Soil sampling location | Source | Reduction (%)[1] |
| --- | --- | --- | --- | --- |
| JHA60 | Ochrobactrum anthropi | Tochigi Pref. | Rhizospheric soil | 37.1**[3] |
| JHB14 | Alcaligenes xylosoxidans | Tochigi Pref. | Rhizospheric soil | 34.7** |
| JHC10 | Alcaligenes faecalis | Iwate Pref. | Rhizospheric soil | 29.2** |
| JHG2 | Ralstonia mannitolilytica | Aomori Pref. | Soil | 27.8*[2] |
| JHJ6 | Cupriavidus necator | Yamagata Pref. | Soil | 35.0** |
| JHL8 | Ralstonia mannitolilytica | Akita Pref. | Soil | 28.7* |
| JHP30 | Ralstonia pickettii | Yamagata Pref. | Rhizospheric soil | 33.3** |
| JHP31 | Variovorax paradoxus | Yamagata Pref. | Rhizospheric soil | 38.5** |
| JHP55 | Ralstonia pickettii | Yamagata Pref. | Rhizospheric soil | 32.5** |

[1]Reduction: (Cd concentration in leaf of control − Cd concentration in leaf of bacterial treatment)/Cd concentration in leaf of control × 100

[2]Significant difference of 5% compared with the control shown via t-test

[3]Significant difference of 1% compared with the control shown via t-test

Example 4

Effects of Cadmium Reduction in Leaves in Field I

The bacteria exhibiting the effects of cadmium reduction in leaves in a greenhouse were subjected to inspection of the effects of cadmium reduction in the field. Four bacterial strains shown in Table 13 were tested in this experiment.

Inoculums were prepared in the same method as in Example 2 except that the cultured bacteria were inoculated into a 500-ml triangular flask containing 200 ml of TS broth.

A tobacco variety, Taihei, was used in this experiment. On the day before transplantation to the field, the bottom of tobacco seedlings grown in vinyl pots (36×36 holes) was subjected to perfusion with 500 ml of the bacterial culture solution (bacteria concentration: $10^9$ to $10^{10}$ cfu/ml; amount of bacteria used per strain: $10^{10}$ to $10^{11}$ cfu) per 36 strains. As a control, seedlings treated with sterile TS broth were used.

Sampling was carried out as follows. Leaves were sampled from the middle leaf position 60 days after transplanting. Three leaves of cutter position from three tobacco plants were sampled as a sample (9 leaves in total). The sampled leaves (whole leaves) were dried at 60° C. to 70° C., ground, and designated as samples for analysis. In this experiment, four samples were prepared for each bacterial treatment and for the control.

The cadmium concentrations in leaves were analyzed in the same method as in Example 2.

The results of the field test are shown in Table 13.

The highest cadmium content in leaves was observed in the control, at 6.28 ppm. The cadmium concentrations in leaves treated with the JHA60 strain, the JHB14 strain, the JHG2 strain, and the JHJ6 strain were 5.33 ppm, 5.20 ppm, 5.12 ppm, and 5.19 ppm, respectively, which were lower than that of the control. Compared with the control, the JHA60 strain, the JHB14 strain, the JHG2 strain, and the JHJ6 strain reduced the cadmium concentrations in leaves by 15.0%, 17.2%, 18.4%, and 17.4%, respectively compared with the control.

TABLE 13

Effects of bacteria for reducing cadmium content in leaf in field

| Treatment group (Strain number) | Bacteria | Cadmium concentration (ppm) | Reduction (%) |
| --- | --- | --- | --- |
| Control | Non | 6.28 | — |
| JHA60 | Ochrobactrum anthropi | 5.33 | 15.0 |
| JHB14 | Alcaligenes xylosoxidans | 5.20 | 17.2 |
| JHG2 | Ralstonia mannitolilytica | 5.12 | 18.4 |
| JHJ6 | Cupriavidus necator | 5.19 | 17.4 |

The above results suggest that the cadmium concentration in tobacco leaves would be lowered via bacterial treatment in the field as well as in a greenhouse. The results also suggest that such bacteria may have the capacity for reducing the cadmium concentration in tobacco leaves.

Example 5

Identification of Bacteria that Reduce Cadmium Content in Plant

The nine cadmium-reducing bacteria selected in Example 3 were identified. We commissioned the Japan Food Research Laboratories to identify the bacteria, and the following identification test was carried out.

(i) Identification with Mycological Properties Based on Morphological and Bacteriological Properties A morphological and bacteriological properties were inspected via microscope observation and bacteriological testing, respectively.

(ii) Identification Using Identification Kit and Via Additional Testing

Bacteria were identified using a kit for identifying gram-negative rod-shaped bacteria (API20NE; manufactured by BioMe'rieux). Additional testing was carried out according to need.

(ii) Identification with 16S rRNA

DNAs of bacteria were extracted, and nucleotide sequences of DNA in the 16S rRNA sequence were analyzed via PCR using the ABI PRISM 310 Genetic Analyzer (Applied Biosystems). The obtained sequences were subjected to homology comparison with the sequences registered in the International Nucleotide Sequence Information Database (DDBJ/EMBL/GenBank) and the database of the MicroSeq ID Analysis Software Version 2.0 (Applied Biosystems), and a dendrogram thereof with the related species was prepared via the neighbor-joining method.

The results of identification of bacteria via mycological properties are as shown in Tables 1 to 9 above.

Example 6

Effects of Cadmium Reduction in Leaves in Field II

Bacteria exhibiting the effects of cadmium reduction in tobacco leaves in a greenhouse were subjected to inspection of the effects of cadmium reduction in the field. The nine strains shown in Table 14 below were tested in this experiment.

Inoculums were prepared in the same method as in Example 2 except that the bacteria were inoculated into a 500-ml triangular flask containing 200 ml of TS broth.

A tobacco variety, Taihei, was used in this experiment. The bacterial treatment to tobacco seedlings was carried out in the same method as in Example 4.

Sampling was carried out as follows. As a sample, three leaves of cutter position were sampled from three tobacco plants 75 days after the transplantation to the field (9 leaves in total). Midribs were removed from the sampled leaves and the mesophylls (laminae) were sampled, dried at 60° C. to 70° C., ground, and designated as samples for analysis. In this experiment, four samples were prepared for each bacterial treatment and for the control.

The cadmium concentrations in leaves were analyzed in the same method as in Example 2.

The results of the field test are shown in Table 14.

The cadmium content in leaves of the control was 6.44 µg/g. Among the nine strains tested in the field, four strains exhibited cadmium reduction of 20% or higher and other 4 strains exhibited reduction of 10% to 20%.

TABLE 14

Effects of cadmium reduction in leaves via treatment with bacteria in field

| Treatment group | Average concentration (µg/g) | Reduction (%) |
| --- | --- | --- |
| JHA60 | 5.86 | 9.1 |
| JHB14 | 5.44 | 15.5 |
| JHC10 | 5.50 | 14.6 |

TABLE 14-continued

Effects of cadmium reduction in leaves
via treatment with bacteria in field

| Treatment group | Average concentration (μg/g) | Reduction (%) |
|---|---|---|
| JHG2 | 5.54 | 14.0 |
| JHJ6 | 5.12 | 20.4 |
| JHL8 | 4.94 | 23.2 |
| JHP30 | 5.21 | 19.1 |
| JHP31 | 5.01 | 22.2 |
| JHP55 | 5.05 | 21.6 |
| Control group | 6.44 | — |

Average concentration: Average concentration of 4 samples; samples: mesophylls

Example 7

Frequency of Bacterial Treatment and Effects of Cadmium Reduction

The effect of the frequency of bacterial treatment on cadmium reduction was inspected. A burley tobacco variety, Taihei, was used in this experiment. This experiment was conducted in the field. Five bacterial strains shown in Table 15 were tested in this experiment.

In this experiment, treatment was carried out once or twice. As the group that was treated once, tobacco seedlings that had been subjected to perfusion with the bacterial culture solution (bacteria concentration: $10^9$ to $10^{10}$ cfu/ml; amount of bacteria used per strain: $10^{10}$ to $10^{11}$ cfu) on the day before being transplanted to the field in the same method as in Example 6, were used. The group that was treated twice was subjected to perfusion thereof at the bottom with 200 ml of the bacterial culture solution (bacteria concentration: $10^7$ to $10^8$ cfu/ml; amount of bacteria used per strain: $10^{10}$ to $10^{11}$ cfu) 35 days after transplantation to the field, in addition to the first treatment.

As a sample, three leaves of cutter position were sampled from three tobacco plants 70 days after transplantation to the field (9 leaves in total). Midribs were removed from the sampled leaves and the mesophylls (laminae) were sampled, dried at 60° C. to 70° C., ground, and designated as samples for analysis. In this experiment, four samples were prepared for the group that was treated once and three samples were prepared for the group that was treated twice.

The cadmium concentrations in leaves were analyzed in the same method as in Example 2.

The results of the field test are shown in Table 15.

The cadmium content in leaves of the control was 6.15 μg/g in the field. On all the tested bacterial strains, leaves sampled from tobacco plants treated twice with bacteria exhibited higher percentages of reduction than those from tobacco plants treated once.

TABLE 15

Frequency of treatment and effects of cadmium reduction

| Control group | Frequency of treatment | Average concentration (μg/g) | Reduction (%) |
|---|---|---|---|
| JHB14 | Once | 5.25 | 14.7 |
| | Twice | 4.45 | 27.6 |
| JHC10 | Once | 5.54 | 9.9 |
| | Twice | 4.48 | 27.2 |

TABLE 15-continued

Frequency of treatment and effects of cadmium reduction

| Control group | Frequency of treatment | Average concentration (μg/g) | Reduction (%) |
|---|---|---|---|
| JHG2 | Once | 5.19 | 15.5 |
| | Twice | 4.69 | 23.7 |
| JHJ6 | Once | 4.91 | 20.2 |
| | Twice | 4.55 | 26.0 |
| JHP31 | Once | 4.89 | 20.4 |
| | Twice | 3.29 | 46.5 |
| Control group | | 6.15 | — |

Average concentration: Average concentration of 4 samples; samples: mesophylls

Example 8

Soil Type and Effects of Cadmium Reduction

The influence of soil type on the effects of cadmium reduction was inspected. This experiment was carried out in a greenhouse with the use of a tobacco variety, Tsukuba 1. The JHJ6 strain, the JHL8 strain, and the JHP31 strain were tested in this experiment.

Inoculums were prepared in the same method as in Example 2.

Two types of soil (i.e., a volcanic ash soil and a sandy soil) were tested in this experiment. JT organic/chemical fertilizers for flue-cured tobacco were mixed with volcanic ash soil or sandy soil at a proportion of 100:1 by weight, and a cadmium chloride solution was then added as with the case of Example 2.

Sampling and analysis of the cadmium concentrations in samples were carried out in the same method as in Example 2. In this experiment, four samples were prepared for each bacterial treatment and for the control.

The results of the experiment are shown in Table 16.

The cadmium concentrations in tobacco leaves of the tested JHJ6, JHL8, and JHP31 strains were lower than that of the control by at least 20% both in the volcanic ash soil and in the sandy soil.

TABLE 16

Soil type and effects of cadmium reduction

| Soil type | Treatment group | Average concentration (μg/g) | Reduction (%) |
|---|---|---|---|
| Volcanic ash soil | JHJ6 | 13.29 | 22.5 |
| | JHL8 | 12.58 | 26.7 |
| | JHP31 | 12.53 | 27.0 |
| | Control group | 17.15 | — |
| Sandy soil | JHJ6 | 14.51 | 26.2 |
| | JHL8 | 14.03 | 28.7 |
| | JHP31 | 14.75 | 25.0 |
| | Control group | 19.67 | — |

Average concentration: Average concentration in leaves of 4 samples; samples: leaves Example 9

Bacteria Concentration and Effects of Cadmium Reduction

The influence of the concentration of bacteria to be applied on the effects of cadmium reduction was inspected. This experiment was carried out in a greenhouse with the use of a tobacco variety, Tsukuba 1. The JHJ6 strain, the JHL8 strain, and the JHP31 strain were tested in this experiment.

Solutions of the bacteria diluted to $10^9$, $10^8$, and $10^7$ cfu/ml, respectively, were prepared as the inoculums, and the seedlings were subjected to perfusion thereof at the bottom with such bacterial solutions on the day before transplantation.

Sampling and analysis of the cadmium concentration in samples were carried out in the same method as in Example 2. In this experiment, four samples were prepared for the groups treated with bacteria of different concentrations and for the control.

The results of the experiment are shown in Table 17.

JHJ6, JHL8, and JHP31 strains used in this experiment reduced the cadmium concentrations in leaves compared with the control. The cadmium concentrations in leaves sampled from of the tobacco plants treated with bacterial solutions of different concentrations were lower than that of the control by at least 10%. The percentage of reduction caused by the bacterial strains was likely to increase with higher bacteria concentration.

TABLE 17

Concentration of bacteria and effects of cadmium reduction

| Treatment group | Concentration of bacteria (cfu/ml) | Average concentration (µg/g) | Reduction (%) |
| --- | --- | --- | --- |
| JHJ6 | $1.4 \times 10^9$ | 17.37 | 21.5 |
|  | $1.4 \times 10^8$ | 16.90 | 23.6 |
|  | $1.4 \times 10^7$ | 18.25 | 17.5 |
| JHL8 | $1.2 \times 10^9$ | 15.07 | 31.9 |
|  | $1.2 \times 10^8$ | 15.64 | 29.3 |
|  | $1.2 \times 10^7$ | 17.27 | 21.9 |
| JHP31 | $3.9 \times 10^9$ | 16.08 | 27.3 |
|  | $3.9 \times 10^8$ | 16.86 | 23.8 |
|  | $3.9 \times 10^7$ | 17.41 | 21.3 |
| Control group |  | 22.12 | — |

Average concentration: Average concentration in leaves of 4 samples; samples: leaves Example 10

Effects of Cadmium Reduction in Tomato

The effects of cadmium reduction in tomatoes were inspected in a greenhouse.

Inoculums were prepared in the same method as in Example 2. Seven strains shown in Table 18 were tested in this experiment.

A grape tomato variety (*Puchi eeru*, Tohoku Seed Co., Ltd.) was tested. The seedlings obtained via sowing in greenhouse molds and cultivation for 30 days were transplanted to soil supplemented with cadmium that had been prepared in the same method as in Example 2.

Five to seven fruits were sampled from two tomato plants 70 days after transplantation, and fruits sampled from a single plant were collectively designated as a sample (12 to 14 fruits). The sample was freeze-dried, ground, and designated as a sample for analysis. In this experiment, four samples were prepared for each bacterial treatment and for the control.

The cadmium concentrations in the samples were analyzed in the same method as in Example 2.

The results of the experiment are shown in Table 18.

Among the 7 tested strains, 6 strains exhibited reduction of 20% or higher compared with the cadmium concentration of the control.

TABLE 18

Effects of cadmium reduction in tomato

| Treatment group | Average concentration (µg/g) | Reduction (%) |
| --- | --- | --- |
| JHP31 | 2.72 | 26.3 |
| JHG2 | 3.02 | 18.1 |
| JHC10 | 2.48 | 32.9 |
| JHA60 | 2.87 | 22.4 |
| JHP30 | 2.77 | 25.0 |
| JHP55 | 2.68 | 27.4 |
| JHL8 | 2.91 | 21.0 |
| Control | 3.69 | — |

Average concentration: average concentration of 4 samples; samples: fruits

Example 11

Effects of Cadmium Reduction in Capsicum

The effects of cadmium reduction in capsicum were inspected in a greenhouse. Five strains shown in Table 19 were tested in this experiment.

Inoculums were prepared in the same method as in Example 2.

A capsicum variety (Takanotsume) was tested. The purchased capsicum seedlings were transplanted to soil supplemented with cadmium that had been prepared in the same method as in Example 2.

Ten to fifteen fruits were sampled from the capsicum strains 80 days after transplantation and collectively designated as a sample. Each sample was freeze-dried, ground, and designated as a sample for analysis. In this experiment, four samples were prepared for each bacterial treatment and for the control.

The cadmium concentrations in the samples were analyzed in the same method as in Example 2.

The results of the experiment are shown in Table 19.

Among the 5 tested strains, 3 strains exhibited reduction of 30% or higher and 2 strains exhibited reduction of 20% to 30% compared with the cadmium concentration of the control.

TABLE 19

Effects of cadmium reduction in capsicum

| Treatment group | Average concentration (µg/g) | Reduction (%) |
| --- | --- | --- |
| JHB14 | 4.80 | 36.2 |
| JHJ6 | 5.93 | 21.3 |
| JHP31 | 4.47 | 40.7 |
| JHG2 | 5.91 | 21.6 |
| JHC10 | 3.35 | 55.5 |
| Control | 7.53 | — |

Average concentration: average concentration of 4 samples; samples: fruits

Example 12

Effects of Cadmium Reduction in Soybean

The effects of cadmium reduction in soybean were inspected in a greenhouse. This experiment was carried out in a greenhouse.

Inoculums were prepared in the same method as in Example 2. Nine strains shown in Table 20 were tested in this experiment.

As a soybean sample, an early green soybean variety (*Hakucho*, Tohoku Seed Co., Ltd.) was tested. The seedlings obtained via sowing in vinyl pots and cultivation for 30 days were transplanted to soil supplemented with cadmium that had been prepared in the same method as in Example 2.

Five to eight pods were sampled from the two soybean strains 45 days after transplantation, and the pods sampled from a single strain were collectively designated as a sample. The samples were dried at 60° C. to 70° C. and beans (30 beans/sample) were extracted from pods. The samples were separately ground and designated as samples for analysis. In this experiment, four samples were prepared for each bacterial treatment and for the control.

The cadmium concentrations in the samples were analyzed in the same method as in Example 2.

The results of the experiment are shown in Table 20.

Among the 9 tested strains, 6 strains exhibited cadmium concentration reduction of 30% or higher, 2 strains exhibited cadmium concentration reduction of 20% to 30%, and one strain exhibited cadmium concentration reduction of 15% to 20%, compared with the cadmium concentration of the control.

TABLE 20

Effects of cadmium reduction in soybean

| Treatment group | Average concentration (µg/g) | Reduction (%) |
| --- | --- | --- |
| JHB14 | 1.13 | 16.7 |
| JHJ6 | 0.88 | 35.3 |
| JHP31 | 0.90 | 33.7 |
| JHG2 | 0.91 | 33.0 |
| JHC10 | 0.93 | 31.1 |
| JHA60 | 1.07 | 21.2 |
| JHP30 | 0.94 | 31.0 |
| JHP55 | 0.93 | 31.6 |
| JHL8 | 0.98 | 27.6 |
| Control | 1.36 | — |

Average concentration: average concentration of 4 samples; samples: beans

Example 13

Effects of Cadmium Reduction in *Brassica chinensis komatsuna*

The effects of cadmium reduction in *Brassica chinensis komatsuna* were inspected in a greenhouse. Five strains shown in Table 21 were tested in this experiment.

Inoculums were prepared in the same method as in Example 2.

As the *Brassica chinensis komatsuna* sample, a Komatsuna variety (Sakata Seed Corporation) was tested. A garden planter (length×width×height: 40 cm×16.5 cm×16 cm) was filled with soil supplemented with cadmium (6 kg, volume: 6 liters), and seeds of *Brassica chinensis komatsuna* were sowed therein. A bacterial solution (200 ml) was applied thereto 15 days after sowing.

The terrestrial parts of the *Brassica chinensis komatsuna* strains were sampled 30 days after application of the bacterial solution, two strains were collectively designated as a sample, and the samples were dried at 60° C. to 70° C., separately ground, and designated as samples for analysis. In this experiment, four samples were prepared for each bacterial treatment and for the control.

The cadmium concentrations in the samples were analyzed in the same method as in Example 2.

The results of the experiment are shown in Table 21.

Among the 5 tested strains, 2 strains exhibited cadmium concentration reduction of 20% or higher and 2 strains exhibited cadmium concentration reduction of 10% to 20%, compared with that of the control.

TABLE 21

Effects of cadmium reduction in *Brassica chinensis komatsuna*

| Treatment group | Average concentration (µg/g) | Reduction (%) |
| --- | --- | --- |
| JHB14 | 1.30 | 24.4 |
| JHP31 | 1.43 | 17.2 |
| JHC10 | 1.42 | 17.4 |
| JHA60 | 1.57 | 8.9 |
| JHP55 | 1.22 | 29.2 |
| Control | 1.72 | — |

Average concentration: average concentration of 4 samples; samples: terrestrial parts Example 14

Influence of Bacteria Treatment on Heavy Metals Other than Cadmium

This experiment was conducted in the field. The burley variety, Taihei, was used in this experiment.

Inoculums were prepared in the same method as in Example 6. Perfusion was carried out in the same method as in Example 4. Sampling and preparation of samples were carried out in the same method as in Example 6. Analysis of heavy metal concentrations in leaves was carried out by the method described in Example 2, as with the case of analysis of cadmium concentrations.

The results of the field tests of the JHJ6, JHL8, and JHP31 strains are shown in Table 22.

Cu (copper): the 3 tested strains exhibited copper concentration reduction of 10% or higher, compared with that of the control.

Pb (lead): one out of the 3 tested strains exhibited lead concentration reduction of 20% or higher and two strains exhibited lead concentration reduction of 10% to 20%, compared with that of the control.

Cr (chromium): two out of the 3 tested strains exhibited chromium concentration reduction of 20% or higher and one strain exhibited chromium concentration reduction of 10% to 20%, compared with that of the control.

Ni (nickel): two out of the 3 tested strains exhibited nickel concentration reduction of 10% or higher, compared with that of the control.

As (arsenic): two out of the 3 tested strains exhibited arsenic concentration reduction of 20% or higher and one strain exhibited arsenic concentration reduction of 10% to 20%, compared with that of the control.

TABLE 22

Influence on heavy metals other than cadmium

| Treatment group | Heavy metal | Average concentration (µg/g) | Reduction (%) |
| --- | --- | --- | --- |
| JHJ6 | Cu | 23.41 | 15.1 |
| JHL8 |  | 23.46 | 14.9 |
| JHP31 |  | 22.94 | 16.8 |
| Control |  | 27.57 | — |

TABLE 22-continued

Influence on heavy metals other than cadmium

| Treatment group | Heavy metal | Average concentration (μg/g) | Reduction (%) |
|---|---|---|---|
| JHJ6 | Pb | 1.09 | 22.5 |
| JHL8 |  | 1.18 | 16.0 |
| JHP31 |  | 1.17 | 16.7 |
| Control |  | 1.40 | — |
| JHJ6 | Cr | 1.39 | 23.1 |
| JHL8 |  | 1.33 | 26.3 |
| JHP31 |  | 1.47 | 18.9 |
| Control |  | 1.81 | — |
| JHJ6 | Ni | 1.41 | 8.9 |
| JHL8 |  | 1.26 | 18.2 |
| JHP31 |  | 1.31 | 14.9 |
| Control | As | 1.54 | — |
| JHJ6 |  | 0.20 | 25.0 |
| JHL8 |  | 0.21 | 21.0 |
| JHP31 |  | 0.23 | 13.7 |
| Control |  | 0.27 |  |

Average concentration: average concentration in leaves of 4 samples; samples: mesophylls All publications, patents, and patent applications cited herein are incorporated herein by reference in their entirety.

The invention claimed is:

1. An isolated bacterium which is selected from the group consisting of *Ochrobactrum anthropi* JHA60 strain (Accession Number: NITE BP-549), *Alcaligenes xylosoxidans* JHB14 strain (Accession Number: NITE BP-550), *Alcaligenes faecalis* JHC10 strain (Accession Number: NITE BP-551),*Ralstonia mannitolilytica* JHG2 strain (Accession Number: NITE BP-552), *Ralstonia mannitolilytica* JHL8 strain(Accession Number: NITE BP-554), *Ralsionia pickettii* JHP30 strain (Accession Number: NITE BP-555), *Ralstonia pickettii* JHP55 strain (Accession Number: NITE BP-557), *Variovorax paradoxus* JHP31 strain (Accession Number: NITE BP-556), and *Cupriavidus necator* JHJ6 strain (Accession Number: NITE BP-553) and has a function of reducing the content of heavy metals in a plant and has a colonization to a root of the plant.

2. The isolated bacterium according to claim 1, wherein the heavy metal is selected from the group consisting of cadmium, copper, lead, chromium, nickel, and arsenic.

3. The isolated bacterium according to claim 1 or 2, which is immobilized on a carrier.

4. A composition for reducing the content of heavy metals in a plant comprising, as an active ingredient, the isolated bacterium according to claim 1.

5. A method for reducing the content of heavy metals in a plant comprising applying at least one bacterium according to claim 1 to a root of a plant or soil around plant roots at least once during the period from sowing to post-transplanting in the field.

6. The method according to claim 5, wherein the applying is carried out by directly applying the bacterium to the root, or by adding or mixing the bacterium to/with soil around the root or to/with a hydroponic solution.

7. The method according to claim 5 or 6, wherein the plant is selected from the group consisting of plants of Solanaceae, Gramineae, Polygonaceae, Leguminosae, Brassicaceac, Liliaceae, Compositae, and Chenopodiaceae families.

8. The isolated bacterium according to claim 1, wherein the bacterium is *Variovorax paradoxus* JHP31 strain (Accession Number: NITE BP-556).

* * * * *